United States Patent
Luo et al.

(10) Patent No.: US 11,639,474 B2
(45) Date of Patent: May 2, 2023

(54) CATALYTIC CRACKING PROCESS AND CATALYST SYSTEM THEREFOR

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Yibin Luo, Beijing (CN); Ying Ouyang, Beijing (CN); Enhui Xing, Beijing (CN); Xingtian Shu, Beijing (CN); Xiaojie Cheng, Beijing (CN); Genquan Zhu, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

( * ) Notice: Subject to any disclaimer, the term of this patent is extended or adjusted under 35 U.S.C. 154(b) by 0 days.

(21) Appl. No.: 17/288,288

(22) PCT Filed: Oct. 25, 2019

(86) PCT No.: PCT/CN2019/113235
§ 371 (c)(1),
(2) Date: Apr. 23, 2021

(87) PCT Pub. No.: WO2020/083363
PCT Pub. Date: Apr. 30, 2020

(65) Prior Publication Data
US 2021/0395616 A1    Dec. 23, 2021

(30) Foreign Application Priority Data

Oct. 26, 2018   (CN) .......................... 201811261409.3

(51) Int. Cl.
| | | |
|---|---|---|
| *C10G 11/05* | (2006.01) | |
| *B01J 29/40* | (2006.01) | |
| *C07C 4/06* | (2006.01) | |
| *C08G 83/00* | (2006.01) | |

(52) U.S. Cl.
CPC .............. *C10G 11/05* (2013.01); *B01J 29/40* (2013.01); *C07C 4/06* (2013.01); *C08G 83/003* (2013.01); *C08G 83/005* (2013.01); *C07C 2529/40* (2013.01); *C10G 2300/1074* (2013.01); *C10G 2300/202* (2013.01); *C10G 2300/301* (2013.01); *C10G 2300/302* (2013.01); *C10G 2300/308* (2013.01); *C10G 2300/4006* (2013.01); *C10G 2300/4018* (2013.01); *C10G 2400/02* (2013.01); *C10G 2400/04* (2013.01); *C10G 2400/20* (2013.01)

(58) Field of Classification Search
CPC ............ C10G 11/05; C10G 2300/1074; C10G 2300/202; C10G 2300/301; C10G 2300/302; C10G 2300/308; C10G 2300/4006; C10G 2300/4018; C10G 2400/02; C10G 2400/04; C10G 2400/20; B01J 29/40; C07C 4/06; C07C 2529/40; C07C 2529/70; C07C 11/04; C07C 11/06; C07C 11/08; C08G 83/003; C08G 83/005
See application file for complete search history.

(56) References Cited

FOREIGN PATENT DOCUMENTS

| | | |
|---|---|---|
| CN | 1085885 A | 4/1994 |
| CN | 102268127 B | 11/2012 |
| CN | 107814675 A | 3/2018 |
| CN | 108002971 A | 5/2018 |
| EA | 17251 B1 | 11/2012 |
| RU | 2525470 C2 | 8/2014 |

OTHER PUBLICATIONS

Hawker, C. J. et al.; One-Step Synthesis of Hyperbranched Dendritic Polyesters, Journal of American Chemical Society, vol. 113, No. 12, 1991, 4583-4588.
He, Guijin et al.; Palmitoyl hyperbranched Polyglycerol as a nanoscale initiator for endothermic hydrocarbon fuels, Fuel, (161) 2015, 295-303.
Yang, Cuiding et al.; Petrochemical analysis methods (RIPP test method), RIPP 92-90 method, Science Press, 1990, pp. 263-268.
One-Step Synthesis of Hyperbranched Dendritic Polyesters, C. J. Hawker et al., J. Am. Chem. Soc., vol. 113, No. 12, 1991, 5 4583-4588.
Controlled Synthesis of Hyperbranched Polyglycerols by Ring-Opening Multibranching Polymerization, Alexander Sunder et. al., Macromolecules, 1999, 32, 4240-4246 :fP One-Step Synthesis of Hyperbranched Dendritic Polyesters, C. J. Hawker et al., J. Am. Chem. Soc., vol. 113, No. 12, 1991, 4583-4588.
Palmitoyl hyperbranched Polyglycerol as a nanoscale initiator for endothermic hydrocarbon fuels, Gui-jin He et al., Fuel, 2015, 161, 295-303.

(Continued)

*Primary Examiner* — Thuan D Dang
(74) *Attorney, Agent, or Firm* — Novick, Kim & Lee, PLLC; Allen Xue

(57) ABSTRACT

A catalytic cracking process includes a step of contacting a cracking feedstock with a catalytic cracking catalyst in the presence of a radical initiator for reaction under catalytic cracking conditions. The radical initiator contains a dendritic polymer and/or a hyperbranched polymer. The dendritic polymer and the hyperbranched polymer each independently has a degree of branching of about 0.3-1, and each independently has a weight average molecular weight of greater than about 1000. The catalytic cracking process is beneficial to enhancing and accelerating the free radical cracking of petroleum hydrocarbon and promoting the regulation of cracking activity and product distribution; by using the process disclosed herein, the conversion of catalytic cracking can be improved, the yields of ethylene and propylene can be increased, and the yield of coke can be reduced.

12 Claims, 1 Drawing Sheet

(56) References Cited

OTHER PUBLICATIONS

Synthesis, Characterization, and Viscoelastic Properties of High Molecular Weight Hyperbranched Polyglycerols, Rajesh Kumar Kainthan et al., Macromolecules, 2006, 39, 7708-7717.

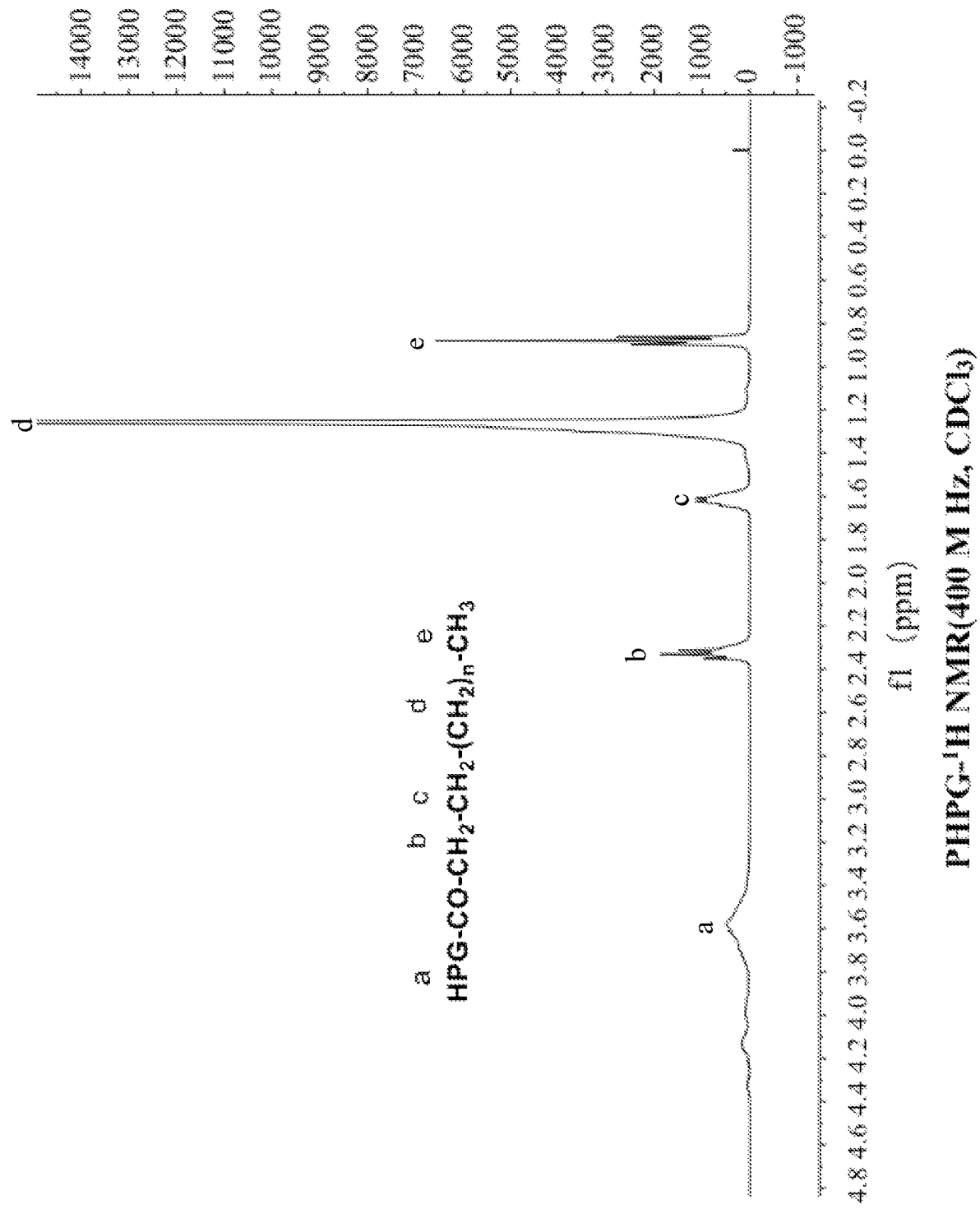

CATALYTIC CRACKING PROCESS AND CATALYST SYSTEM THEREFOR

TECHNICAL FIELD

The present application relates to the field of catalytic cracking, and more particularly to a catalytic cracking process and catalyst system therefor.

BACKGROUND ART

In the 21st century, as the price fluctuation of crude oil and the rapid progress of exploration technology, a trend of diversification and lower cost of global petrochemical raw materials is presented. Particularly, the rapid expansion of petrochemical production capacity in Middle East areas rich in light hydrocarbon resources, the development of North American shale gas industry and Chinese coal chemical industry, and the like, bring huge impact to the traditional petrochemical industry taking naphtha as a raw material. Further, the large-scale marketization of the ethane-to-ethylene conversion technology also poses a challenge to the production of light olefins by steam cracking of naphtha. In comparison, the conventional naphtha route for ethylene production has the defect of high cash cost and low cost competitiveness, so that the development of a competitive chemical material production technology gains more attention.

Cracking of hydrocarbons at high temperatures is an important process for converting long-chain hydrocarbons into short-chain hydrocarbons of high added value, especially light olefins and gasoline, such as catalytic cracking and steam cracking. The catalytic cracking is a complex process for cracking petroleum hydrocarbons at high temperatures by breaking the chains thereof to form olefins and alkanes having small molecules under the action of a catalyst. The reaction mechanism of catalytic cracking is closely related to the type of catalyst and the cracking procedure.

Generally, the mechanism of the cracking of hydrocarbons can be classified into a carbonium ion mechanism (catalytic cracking) and a radical mechanism (steam cracking). The carbonium ion mechanism occurs only under the action of an acidic catalyst, while the free radical mechanism normally occurs under the condition of thermal initiation at a temperature higher than 800° C., with ethylene being a characteristic cracking product. Since the carbonium ion mechanism occurs in the presence of an acidic catalyst, the reaction temperature is relatively low and propylene is a characteristic cracking product.

Generally speaking, in a low temperature cracking process performed on an acidic zeolite catalyst, the reaction mainly occurs following the carbonium ion mechanism. That is, alkanes, alkenes or arenes are initiated by the acidic center on the catalyst to generate a carbonium ion, then the carbonium ion is isomerized and then broken at the β position to generate an alkene; and thereafter, the carbonium ion is desorbed, $H^+$ is returned to the catalyst, the carbonium ion itself is converted into an alkene.

Free radical cracking follows a chain reaction mechanism. The free radical cracking process of hydrocarbons has three stages: initiation of free radicals, transfer of free radicals, and termination of free radicals. Generally, the initiation of free radicals is a rate-controlling step of the cracking reaction, but the initiation of free radicals usually requires a high temperature, so that the effect of regulating the distribution of cracking products by the free radical mechanism is normally significant at a high temperature. A chemical bond is uniformly cracked to obtain two free radicals, and the generated free radicals may undergo hydrogen abstraction, decomposition and addition reactions. The hydrogen abstraction reaction may generate a new free radical, the decomposition reaction may generate an olefin and a new free radical, and the addition reaction with an olefin may generate an alkane. The association between radicals themselves forms a stable molecule, representing the end of the radical reaction. However, since the thermal initiation temperature of radicals is higher than that of the acid-catalyzed carbonium ion mechanism, the regulation of the cracking performance by the radical route is normally possible at high temperatures. Generally, there are three ways of free radical initiation: peroxide, light, heat, and the like. Initiating free radicals at a suitable temperature can modulate the cracking performance. However, when the temperature for free radical initiation is too low, it is often insufficient to initiate the C—C bond cleavage of hydrocarbons; furthermore, the high activity of free radicals may lead to bonding between free radicals, which may also reduce the efficiency of the radical initiator.

Dendritic polymers are a kind of novel highly-branched functional polymers with a symmetrical and radial structure, which are synthesized by repeated propagation reaction, and have a highly-branched molecule with precise structure. It has three distinct characteristics: precise molecular structure, large number of functional groups and a high degree of geometric symmetry. Dendritic polymers are characterized by low viscosity, high solubility, miscibility, and high reactivity.

Hyperbranched polymers are an important branch of dendritic polymers. Such polymers are not perfect dendrimers, but structurally defective polymers. Their molecules have a compact sphere-like structure, small hydrodynamic turning radius, and less molecular chain entanglement, so that the increase of relative molecular weight has minor impact on the viscosity. In addition, their molecules have a plurality of functional terminal groups and can be modified to obtain a functional material.

There remains a need in the art for a process and catalyst system that allows an effective, fine, and free control of the ethylene/propylene ratio in the catalytic cracking product.

SUMMARY OF THE INVENTION

It is an object of the present application to provide a catalytic cracking process and a catalyst system for catalytic cracking reactions that are capable of regulating the cracking activity and product distribution at the catalytic cracking temperature.

To achieve the above objects, in an aspect, the present application provides a catalytic cracking process comprising a step of contacting a cracking feedstock with a catalytic cracking catalyst for reaction in the presence of a radical initiator under catalytic cracking conditions, wherein the radical initiator comprises a dendritic polymer and/or a hyperbranched polymer.

Preferably, the dendritic polymer and the hyperbranched polymer each independently has a degree of branching of about 0.3-1, and the dendritic polymer and the hyperbranched polymer each independently has a weight average molecular weight of greater than about 1000.

Preferably, the ratio of the total weight of dendritic polymer and hyperbranched polymer contained in the radical initiator to the weight of the cracking feedstock is greater than about 0.00001:1.

Preferably, the dendritic polymer and the hyperbranched polymer are each independently selected from the group consisting of polyolefins, polyetheresters, polyethers, polyurethanes, polyamides, polysilanes, or any combination thereof.

Preferably, the catalytic cracking catalyst comprises an acidic zeolite catalyst.

In another aspect, the present application provides a catalyst system for catalytic cracking reactions comprising a radical initiator and a catalytic cracking catalyst, wherein the radical initiator comprises a dendritic polymer and/or a hyperbranched polymer and the catalytic cracking catalyst comprises an acidic zeolite catalyst.

Without being bound to a particular theory, the inventors believe that hydrocarbons may undergo both reactions following the carbonium ion mechanism and reactions following the radical mechanism under catalytic cracking conditions, in which the radical reaction is favorite to the production of ethylene while the carbonium reaction is favorite to the production of propylene and butylene; but since the reaction temperature is relatively lower, the speed of free radical initiation is slow, and the reaction process mainly follows the carbonium ion mechanism, so that the yield of propylene is relatively higher while the yield of ethylene is relatively lower. In the catalytic cracking process disclosed herein, a macromolecular radical initiator is added into a petroleum hydrocarbon catalytic cracking reaction system, whereby a large amount of hydrocarbon molecular free radicals can be uniformly released at a catalytic cracking temperature, and the free radicals uniformly dispersed in hydrocarbons can initiate, enhance and accelerate the free radical cracking of the petroleum hydrocarbon, so that a regulation of the distribution of ethylene/propylene in the product can be revealed while promoting the improvement of cracking activity and yield of light olefins. Therefore, by adopting the catalytic cracking process and catalyst system disclosed herein, the conversion of catalytic cracking and the yield of light olefins can be improved, the yields of ethylene and propylene can be improved at the same time, and the yield of coke can be reduced.

Additional features and advantages of the present application will be described in the detailed description herein below.

BRIEF DESCRIPTION OF THE DRAWINGS

The drawings are provided to help the understanding of the present application, and should be considered as a part of the present description. The present application will be illustrated with reference to the drawings and the embodiments described herein below, which should not be considered to be limiting. In the drawings:

FIG. 1 shows a nuclear magnetic spectrum of a terminal group-modified polyglycidyl ether (PHPG) used in a preferred embodiment of the present application.

DETAILED DESCRIPTION OF THE INVENTION

The present application will now be described in further detail with reference to embodiments thereof and the drawings, and it should be noted that the embodiments described herein are merely provided for the purpose of illustrating and explaining the present application, while are not intended to be restrictive in any manner.

Any numerical value (including the end values of numerical ranges) provided herein is not limited to the precise value recited, but should be interpreted as covering any value close to said precise value, such as all possible values within 5% of said precise value. Moreover, for any numerical range provided herein, one or more new numerical ranges can be obtained by arbitrarily combining the end values of the range, an end value with a specific value provided within the range, or various specific values provided within the range. Such new numerical ranges should also be considered as being specifically disclosed herein.

In the present application, the term "catalyst-to-oil ratio" refers to the weight ratio of catalytic cracking catalyst to cracking feedstock.

Unless otherwise stated, the terms used herein have the same meaning as commonly understood by those skilled in the art; and if the terms are defined herein and their definitions are different from the ordinary understanding in the art, the definition provided herein shall prevail.

In the context of the present application, in addition to those matters explicitly stated, any matter or matters not mentioned are considered to be the same as those known in the art without any change. Moreover, any of the embodiments described herein can be freely combined with another one or more embodiments described herein, and the technical solutions or ideas thus obtained are considered as part of the original disclosure or original description of the present application, and should not be considered to be a new matter that has not been disclosed or anticipated herein, unless it is clear to those skilled in the art that such a combination is obviously unreasonable.

All of the patent and non-patent documents cited herein, including but not limited to textbooks and journal articles, are hereby incorporated by reference in their entirety.

In a first aspect, the present application provides a catalytic cracking process comprising a step of contacting a cracking feedstock with a catalytic cracking catalyst for reaction in the presence of a radical initiator under catalytic cracking conditions.

According to the present application, the radical initiator preferably comprises a dendritic polymer and/or a hyperbranched polymer, wherein the degree of branching of the dendritic polymer and hyperbranched polymer is preferably each independently about 0.3-1, preferably about 0.4-1; the weight average molecular weight of the dendritic polymer and hyperbranched polymer is preferably each independently greater than about 1000, preferably from about 2000 to about 30000, more preferably from about 2000 to about 25000.

In a preferred embodiment, the radical initiator consists of a dendritic polymer and/or a hyperbranched polymer.

As mentioned above, in the catalytic cracking process of the present application, a macromolecular radical initiator is added into a petroleum hydrocarbon catalytic cracking reaction system, wherein the radical initiator comprises a dendritic polymer and/or a hyperbranched polymer. Since a highly branched dendritic polymer and hyperbranched polymer is used, the radical initiator comprises a large number of functional terminal groups, and these numerous branched structures and terminal groups enable the radical initiator to generate a large number of hydrocarbon molecular free radicals under catalytic cracking conditions, which may initiate and further enhance and accelerate the radical cracking of the petroleum hydrocarbon, thereby achieving the purpose of regulating the activity and product distribution. Therefore, the catalytic cracking process disclosed herein can improve the conversion of catalytic cracking, increase the yield of gaseous product, especially light olefins, increase the yield of ethylene and propylene at the same time, and reduce the yield of coke.

In the catalytic cracking process according to the present application, the amount of the radical initiator may vary within a wide range, and in order to obtain better product distribution regulation effect, preferably, the ratio of the total weight of the dendritic polymer and the hyperbranched polymer contained in the radical initiator to the weight of the cracking feedstock may be greater than about 0.00001:1, more preferably about 0.00001:1 to about 0.01:1, such as about 0.00005-0.009:1, about 0.00006-0.008:1, about 0.00007-0.007:1 or about 0.00008-0.006:1, more preferably about 0.0001:1 to about 0.005:1.

In the catalytic cracking process according to the present application, the radical initiator and the cracking feedstock may be fed to the catalytic cracking reaction system together or separately, for example, in an embodiment, the radical initiator and the cracking feedstock may be mixed uniformly first and then the mixed material may be fed into the catalytic cracking reactor; in another embodiment, the radical initiator and the cracking feedstock may be fed into the catalytic cracking reaction system separately from each other, for example, by feeding the radical initiator and the cracking feedstock separately into the catalytic cracking reactor through two separate feed lines.

In the context of the present application, the term "dendritic polymer" has the same meaning well known in the art, and refers to linear polymers with dendritic units on each repeating unit. The term "hyperbranched polymer" also has the same meaning well known in the art, and refers to highly branched but structurally irregular polymers composed of dendritic units, which are not perfect dendrimers, but structurally defective polymers. The degree of branching (DB) of dendritic polymers and hyperbranched polymers refers to the ratio of the total number of dendritic units and terminal units to the total number of all repeating units. There are 3 kinds of repeating units in polymers having a branched structure (i.e. dendritic polymer and hyperbranched polymer), that is, dendritic units, linear units, and terminal units derived from unreacted functional groups.

Hawker et al (One-Step Synthesis of hyperbranched Dendritic Polyesters, C. J. Hawker et al., *J. Am. Chem. Soc.*, Vol. 113, No. 12, 1991, 4583-4588) proposes an equation for the calculation of the degree of branching as follows:

$$DB=(D+T)/(D+L+T),$$

wherein D, T and L respectively represent the proportions of dendritic units, terminal units and linear structural units in the polymer molecules with branched structures; for example, if the degree of branching is 0, the polymer has a linear molecule without dendritic and terminal units; if the degree of branching is about 1, all repeating units are fully branched and the mole fraction of dendritic units and terminal units is about 1. The disclosure of this document is incorporated herein by reference in its entirety.

In the present application, the degree of branching can be determined using $^{13}C$ NMR by the method described in the published document, Controlled Synthesis of hyperbranched Polyglycerols by Ring-Opening Multibranching Polymerization, Alexander Sunder et. al., Macromolecules, 1999, 32, 4240-4246.

According to the present application, the degree of branching of the dendritic polymer is preferably about 1, and the degree of branching of the hyperbranched polymer is preferably not less than about 0.4, more preferably about 0.4-0.9, further preferably about 0.4-0.8, such as about 0.4-0.7, about 0.4-0.6, about 0.5-0.8 and about 0.5-0.7. In the above-described preferred range of the degree of branching, the radical initiator has appropriate solubility and viscosity, and can uniformly generate a large amount of hydrocarbon radicals at the catalytic cracking temperature.

According to the present application, the dendritic polymer and the hyperbranched polymer each independently has a weight average molecular weight of greater than about 1000, preferably from about 2000 to about 30000, more preferably from about 2000 to about 25000, such as about 3000-25000, about 3000-20000, about 5000-20000 and about 5000-15000, so as to ensure that the radical initiator has suitable solubility and viscosity, which is in favor of the contact, mixing and reaction of the radical initiator and the catalytic cracking feedstock. In the present application, the weight average molecular weight of the polymer can be determined by volume exclusion chromatography, for example, by the method of GB/T21864-2008.

According to the present application, the kind of the dendritic polymer and the hyperbranched polymer is not particularly limited and may be a conventional one, for example, the dendritic polymer and the hyperbranched polymer may each be independently selected from the group consisting of polyolefins, polyetheresters, polyethers, polyurethanes, polyamides, polysilanes, or any combination thereof.

In certain preferred embodiments, the dendritic polymer and hyperbranched polymer are each independently selected from the group consisting of polyethers, polyamides, or combinations thereof to further promote the generation of hydrocarbon radicals and enhance the dissolution of radical initiators in the cracking feedstock.

In a further preferred embodiment, the radical initiator comprises a polymer selected from the group consisting of hyperbranched polyglycidyl ethers, terminal group-modified hyperbranched polyglycidyl ethers, dendritic polyamide-amines, hyperbranched polyamide-amines, or any combination thereof. The terminal groups of the hyperbranched polyglycidyl ether comprise a large number of hydroxyl groups, and in order to improve the mixing properties with the cracking feedstock, the terminal hydroxyl groups of the hyperbranched polyglycidyl ether can be modified, for example by esterification and/or mercapto-alkenyl methods. Further preferably, the terminal group of the terminal group-modified hyperbranched polyglycidyl ether may be selected from the group consisting of ester groups having 2-10 carbon atoms, amine group, mercapto group, or any combination thereof. Terminal group modification of hyperbranched polyglycidyl ethers can be carried out by methods described in, for example, the documents Synthesis, Characterization, and Viscoelastic Properties of High Molecular Weight Hyperbranched Polyglycerols, Rajesh Kumar Kainthan et al., Macromolecules, 2006, 39, 7708-7717 and Palmitoyl hyperbranched Polyglycerol as a nanoscale initiator for endothermic hydrocarbon fuels, Gui-jin He et al., Fuel, 2015, 161, 295-303, which are hereby incorporated by reference in their entirety.

In a particularly preferred embodiment, the radical initiator comprises or consists of a palmitate-terminated hyperbranched polyglycidyl ether (PHPG).

In a further preferred embodiment, the palmitate-terminated hyperbranched polyglycidyl ether (PHPG) has a weight average molecular weight of greater than about 1000, more preferably about 1000-30000, further preferably about 2000-20000, especially preferably about 5000-15000, such as about 10000 or 12000; and/or the degree of branching of the palmitate-terminated hyperbranched polyglycidyl ether (PHPG) is about 0.3-1, more preferably about 0.3-0.9, even more preferably about 0.4-0.9, particularly preferably about 0.4-0.8, such as about 0.5 or 0.6.
In a still further preferred embodiment, the palmitate-terminated hyperbranched polyglycidyl ether (PHPG) has the structure represented by the formula (I):
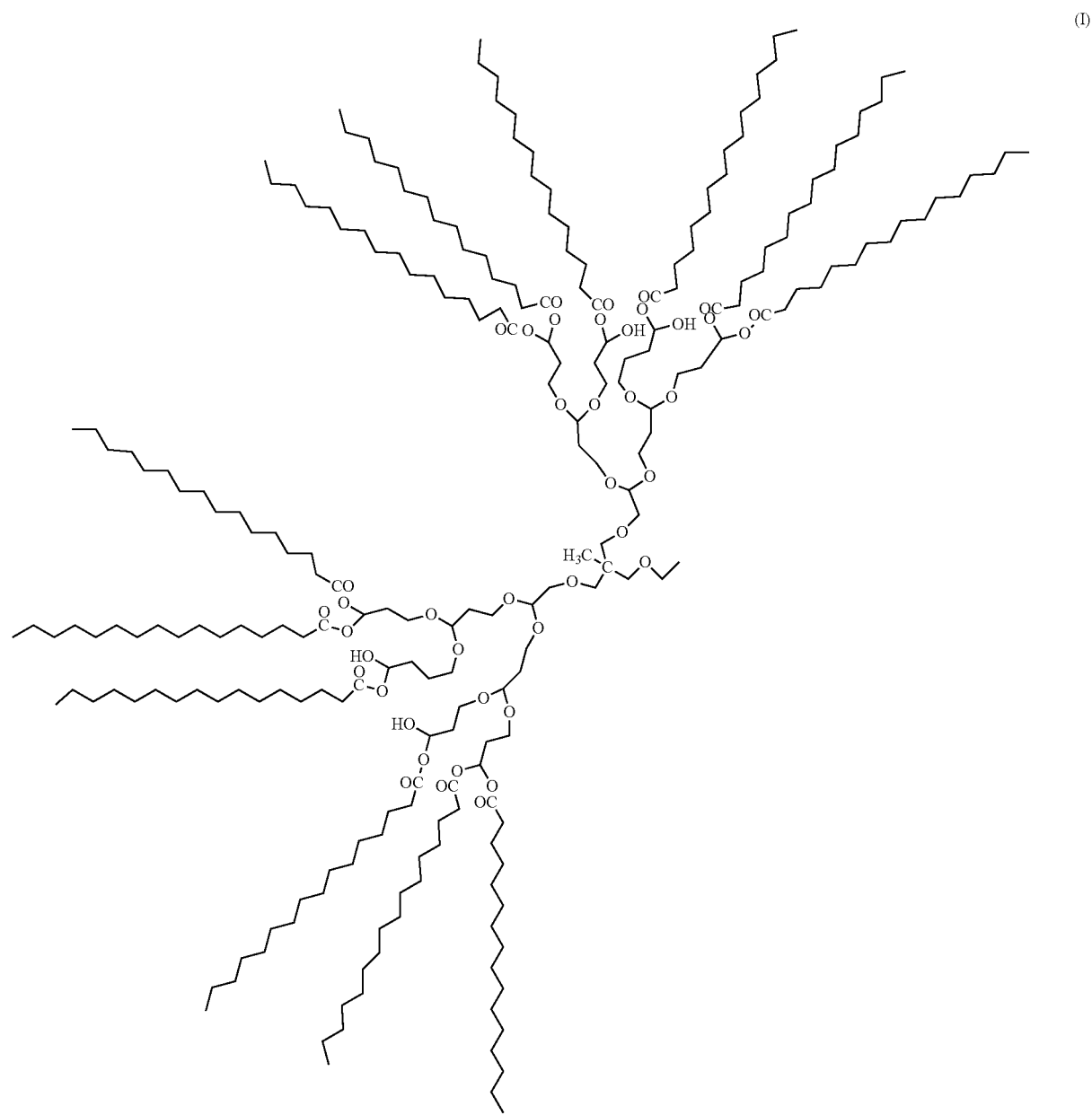

-continued

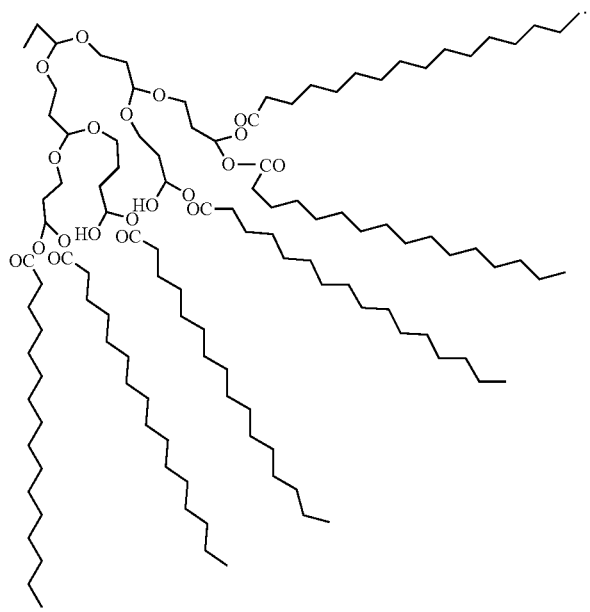

In the present application, catalytic cracking conditions used may be those conventionally used in the art, for example, the catalytic cracking conditions may include: a reaction temperature of about 450-700° C., preferably about 550-650° C., such as about 560° C., 580° C., 600° C., 620° C. or 640° C.; a weight hourly space velocity of about 1-50 $h^{-1}$, preferably about 5-40 $h^{-1}$, such as about 8 $h^{-1}$, 12 $h^{-1}$, 16 $h^{-1}$, 20 $h^{-1}$, 24 $h^{-1}$, 28 $h^{-1}$, 32 $h^{-1}$, or 36 $h^{-1}$; and a catalyst-to- oil ratio of about 1-20, preferably about 1-15, such as about 2, 3, 4, 5, 6, 8, 10, 12 or 14.

In the catalytic cracking process according to the present application, various conventional catalytic cracking feedstocks may be used as the cracking feedstock, and there is no particular limitation in the present application. For example, the cracking feedstock may be selected from the group consisting of hydrocarbons having 4 to 14 carbon atoms, naphtha, light cycle oil, vacuum gas oil, vacuum residuum, or any combination thereof.

In the catalytic cracking process according to the present application, catalysts conventionally used in the field of catalytic cracking may be used, and there is no particular limitation in the present application. In an embodiment of the present application, the catalytic cracking catalyst may be a catalytic cracking catalyst comprising a Y zeolite and/or a shape selective zeolite, to further increase the yield of light olefins, wherein the shape selective zeolite may preferably be selected from the group consisting of ZSM-5 zeolite, β zeolite, or any combination thereof.

In certain particularly preferred embodiments, the catalytic cracking catalyst may comprise about 10-60 wt %, preferably about 20-50 wt %, of a Y zeolite and/or shape selective zeolite, about 5-50 wt %, preferably about 10-40 wt %, of an alumina binder, calculated as alumina, and about 5-60 wt %, preferably about 10-50 wt %, of a clay, calculated on a dry basis.

In the present application, the alumina binder may be one or more selected from various forms of alumina, hydrated alumina, and alumina sol commonly used in catalytic cracking catalysts, for example selected from γ-alumina, η-alumina, θ-alumina, χ-alumina, pseudo-boehmite, boehmite, gibbsite, bayerite or alumina sol or a combination of two, three or four thereof, preferably pseudo-boehmite and alumina sol.

In the present application, the clay may be one or more selected from clays conventionally used as a component of catalytic cracking catalysts, such as kaolin, hydrated halloysite, montmorillonite, diatomite, halloysite, saponite, rectorite, sepiolite, attapulgite, hydrotalcite, or bentonite, or a combination of two, three, or four thereof. These clays are well known in the art.

In a second aspect, the present application provides a catalyst system for catalytic cracking reactions comprising a radical initiator and a catalytic cracking catalyst, wherein the radical initiator comprises a dendritic polymer and/or a hyperbranched polymer and the catalytic cracking catalyst comprises an acidic zeolite catalyst.

In a preferred embodiment, the ratio of the total weight of dendritic polymer and hyperbranched polymer contained in the radical initiator to the weight of the catalytic cracking catalyst is greater than about 0.00001:20, preferably about (0.00001-0.01):(1-20), more preferably about (0.0001-0.005):(1-20), for example about (0.0001-0.005):(1-2).

In this aspect of the present application, other features of the radical initiator and catalytic cracking catalyst are as previously described and will not be described in detail.

In certain preferred embodiments, the present application provides the following technical solutions:

Item 1, a catalytic cracking process, comprising a step of: contacting a catalytic cracking feedstock oil with a catalytic cracking catalyst in the presence of a radical initiator, to carry out a catalytic cracking reaction under catalytic cracking conditions;

the radical initiator comprises a dendritic polymer and/or a hyperbranched polymer, the dendritic polymer and the hyperbranched polymer each independently has a degree of branching of about 0.3-1, and the dendritic polymer and the hyperbranched polymer each independently has a weight average molecular weight of greater than about 1000.

Item 2, the process according to Item 1, wherein the weight ratio of the radical initiator to the catalytic cracking feedstock oil is about (0.00001-0.01):1.

Item 3, the process according to any one of the preceding Items, wherein the process comprises: feeding the radical initiator and the catalytic cracking feedstock oil into a catalytic cracking reaction system together, or feeding the radical initiator and the catalytic cracking feedstock oil into a catalytic cracking reaction system separately.

Item 4, the process according to any one of the preceding Items, wherein the dendritic polymer has a degree of branching of 1 and the hyperbranched polymer has a degree of branching of greater than about 0.4.

Item 5, the process according to any one of the preceding Items, wherein the dendritic polymer and the hyperbranched polymer each independently has a weight average molecular weight of about 3000-30000.

Item 6, the process according to any one of the preceding Items, wherein the dendritic polymer and the hyperbranched polymer are each independently selected from a group consisting of polyolefins, polyetheresters, polyethers, polyurethanes, polyamides, or polysilanes, or a combination of two or three thereof.

Item 7, the process according to any one of the preceding Items, wherein the dendritic polymer and the hyperbranched polymer are each independently polyethers and/or polyamides.

Item 8, the process according to any one of the preceding Items, wherein the radical initiator is a hyperbranched polyglycidyl ether, a terminal group-modified hyperbranched polyglycidyl ether, a dendritic polyamide-amine, a hyperbranched polyamide-amine, or a combination of two or three thereof.

Item 9, the process according to Item 8, wherein the terminal group of the terminal group-modified hyperbranched polyglycidyl ether is selected from ester groups having 2 to 10 carbon atoms, amine group, or mercapto group, or a combination of two or three thereof.

Item 10, the process according to any one of the preceding Items, wherein the catalytic cracking conditions include: a reaction temperature of about 450-700° C., a weight hourly space velocity of about 1-50 h$^{-1}$, and a catalyst-to-oil ratio of about 1-20.

Item 11, the process according to any one of the preceding Items, wherein the catalytic cracking feedstock oil is selected form the group consisting of hydrocarbons having 4 to 14 carbon atoms, naphtha, light cycle oil, vacuum gas oil, vacuum residuum, or a combination of two or three of these.

Item 12, the process according to any one of the preceding Items, wherein the catalytic cracking catalyst is a catalytic cracking catalyst comprising a Y zeolite and a shape selective zeolite.

Item 13, a catalyst system for catalytic cracking reactions, comprising a radical initiator and a catalytic cracking catalyst, wherein the radical initiator comprises a dendritic polymer and/or a hyperbranched polymer and the catalytic cracking catalyst comprises an acidic zeolite catalyst.

Item 14, the catalyst system according to Item 13, wherein the ratio of the total weight of dendritic polymer and hyperbranched polymer contained in the radical initiator to the weight of the catalytic cracking catalyst is greater than about 0.00001:20, preferably about (0.00001-0.01):(1-20), more preferably about (0.0001-0.005):(1-20).

Item 15, the catalyst system according to Item 13 or 14, wherein the catalytic cracking catalyst is a catalytic cracking catalyst comprising a Y zeolite and/or a shape selective zeolite.

Item 16, the catalyst system according to any one of Items 13 to 15, wherein the radical initiator is as defined in any one of Items 2 to 8.

Item 17, the catalyst system according to Item 15, wherein the shape selective zeolite is selected from the group consisting of ZSM-5 zeolite, β zeolite, or any combination thereof.

EXAMPLES

The present application will be further illustrated with reference to the following examples, which are not intended to be limiting. In the following examples of the present application, the reagents used are all commercially available products unless otherwise specified.

The microstructure analysis of the polymer, including the degree of branching, was carried out in accordance with the method described in Controlled Synthesis of hyperbranched Polyglycerols by Ring-Opening Multibranching Polymerization, Alexander Sunder et. al., Macromolecules, 1999, 32, 4240-4246 和 One-Step Synthesis of hyperbranched Dendritic Polyesters, C. J. Hawker et al., *J. Am. Chem. Soc., Vol.* 113, No. 12, 1991, 4583-4588, using 400 MHz NMR instrument from Bruker, Sweden, using deuterated chloroform (CDCl$_3$) or deuterated dimethyl sulfoxide (DMSO-d$_6$) as solvent and tetramethylsilane (TMS) as internal standard.

The molecular weight of the polymer was determined using Modle302TDA Volume Exclusion Chromatograph (SEC/TALLS for short) from Viscotek Corporation, USA, equipped with detectors of Refraction Index (RI), Ultraviolet (UV), Laser Scattering (LS) and viscosity (IV), using tetrahydrofuran (THF) as elution solvent, a flow rate of 1.0 mL/min, a test temperature of 30° C., and OmnisEC 4.5 software for data processing.

Preparation of Radical Initiator

The synthesis of part of the radical initiators used in the examples is briefly described below.

Hyperbranched Polyglycerol (HPG):

A series of hyperbranched polyglycerols (HPGs) with different relative molecular weights were synthesized by an anion ring-opening polymerization method, of which the steps are described in the document Synthesis, Characterization, and Viscoelastic Properties of High Molecular Weight Hyperbranched Polyglycerols, Rajesh Kumar Kainthan et al., Macromolecules, 2006, 39, 7708-7717.

Methanol, trimethylolpropane (TMP) and CH$_3$OK solution were charged into a reaction flask at a predetermined ratio under N$_2$ atmosphere, stirred for 30 min at 50° C., then evacuated to remove the methanol solvent; after that, dioxane was added, heated to a temperature of 95° C., glycidol monomer was slowly added dropwise for 24 h, and then reacted for 12 h after the addition, and finally the resulting product was dissolved with methanol and recrystallized using acetone, which was repeated for 3 times.

Terminal Group-Modified Hyperbranched Polyglycidyl Ether (PHPG):
The terminal hydroxyl groups comprised in hyperbranched polyglycerols (HPGs) were modified through esterification reaction using palmitoyl chloride to obtain a palmitate-terminated hyperbranched polyglycidyl ether (PHPG) represented by the following formula (I),
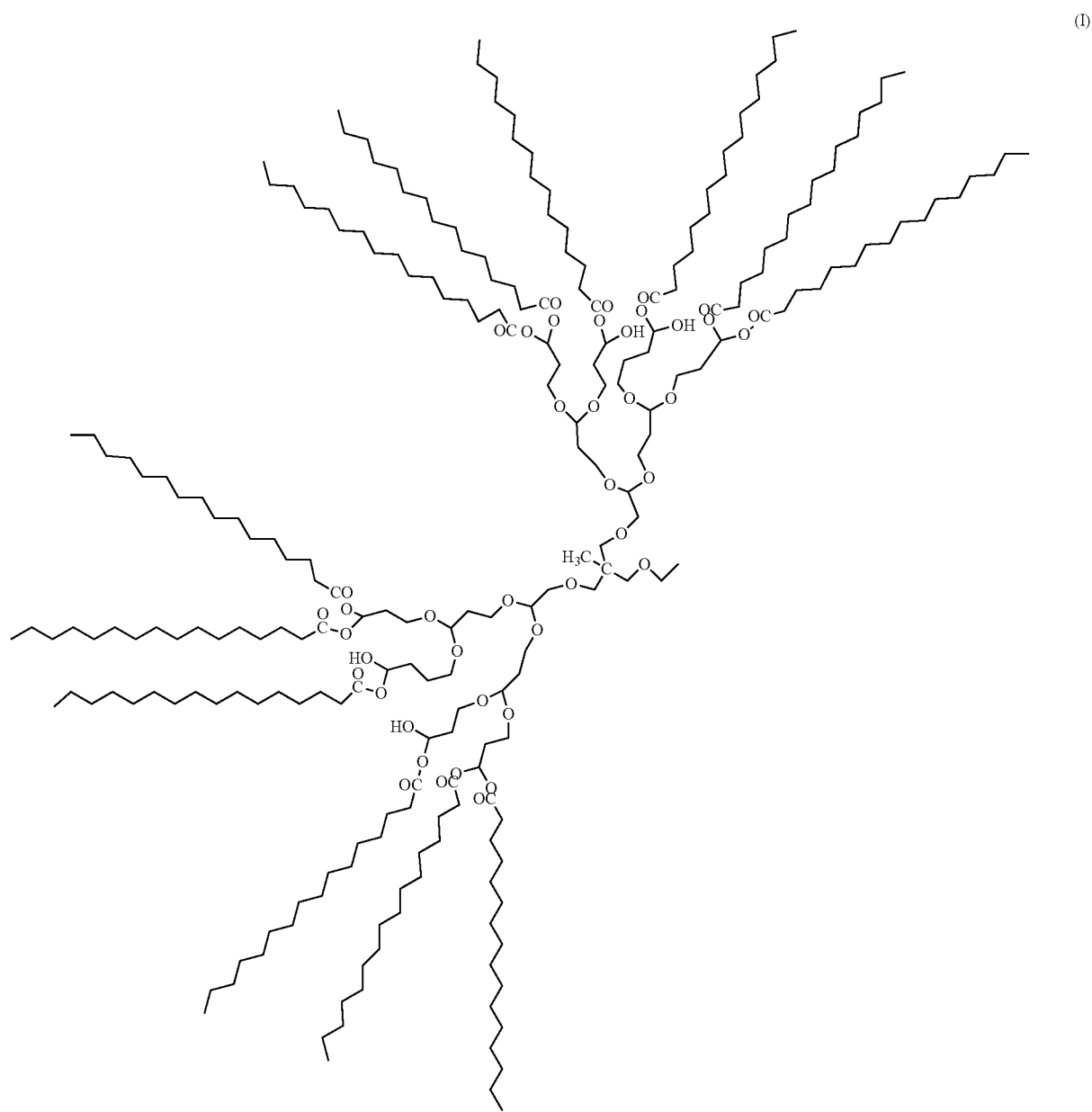
(I)

-continued

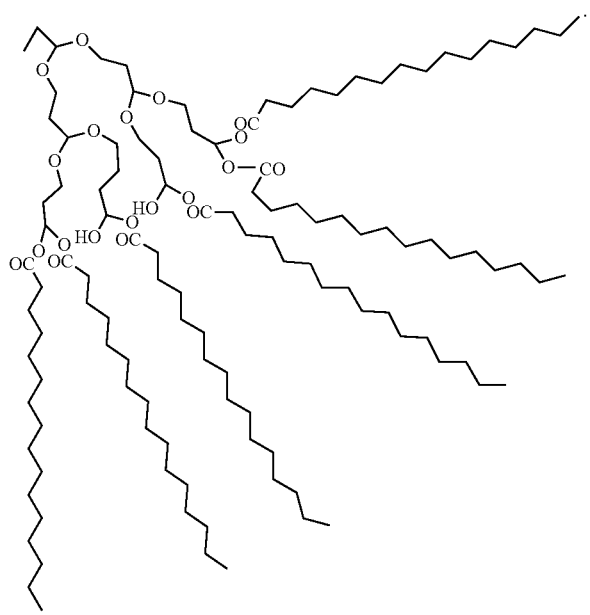

The synthesis process is described in the documents Synthesis, Characterization, and Viscoelastic Properties of High Molecular Weight Hyperbranched Polyglycerols, Rajesh Kumar Kainthan et al., Macromolecules, 2006, 39, 7708-7717 and Palmitoyl hyperbranched Polyglycerol as a nanoscale initiator for endothermic hydrocarbon fuels, Guijin He et al., Fuel, 2015, 161, 295-303.

Palmitoyl chloride was added dropwise into a mixed system of a pyridine solution of polyglycerol at a predetermined ratio under $N_2$ atmosphere, stirred overnight under reflux conditions, concentrated to remove a majority of the pyridine, extracted with dichloromethane, and distilled under reduced pressure to obtain a white waxy solid as the final product, which has a $^1H$ NMR spectrum as shown in FIG. 1, a molecular weight of about 120000 and a degree of branching of 0.5 (i.e., the PHPG of Example 9). PHPGs of different molecular weights and degrees of branching obtained in other examples were synthesized in a similar manner.

Hyperbranched polyamide-amine: prepared in accordance with the method disclosed in CN 102268127B.

Examples 1 to 4

A cracking feedstock (VGO, with properties shown in Table 1) was heated to 90° C. and a radical initiator PHPG was added at an amount shown in Table 2 and mixed uniformly. The radical initiator PHPG has a molecular weight of 10000, and a degree of branching of 0.5.

An activity evaluation was carried out on a micro-activity evaluation device, using a laboratory instrument of WFS-5C Catalytic Micro-activity Tester from DADI Company of Sinopec Research Institute of Petroleum Processing, in accordance with the RIPP 92-90 method (see "Petrochemical analysis methods (RIPP test method)", edited by Cuiding YANG et al., Science Press, 1990, pages 263-268) under the conditions including: a reaction temperature of 650° C., a regeneration temperature of 650° C., a catalyst-to-oil ratio of 1.28, a weight hourly space velocity of 16 $h^{-1}$, an MMC-2 equilibrium catalyst (comprising a modified ZSM-5 zeolite) available from Sinopec Catalyst Co. Ltd., and a catalyst load of 2 g. The evaluation results are shown in Table 2.

TABLE 1

Properties of the cracking feedstock used in Examples 1-17 and Comparative Example 1

| Item | Analytical data |
|---|---|
| Density (20° C.)/g/cm³ | 0.8731 |
| Refractive index (70° C.) | 1.4682 |
| Viscosity (80° C.)/mm²/s | 17.56 |
| Vacuum distillation range/° C. | |
| Initial boiling point | 189 |
| 5% | 398 |
| 10% | 418 |
| 30% | 457 |
| 50% | 497 |
| 70% | 549 |
| 90% | 73.5%, 560° C. |
| Acid value/mgKOH/g | 0.07 |
| Residual carbon/% | 0.7 |
| Ash content/% | 0.05 |
| S content/% | 0.12 |
| N content/% | 0.11 |
| Contents of C and H/% | |
| C | 86.43 |
| H | 13.53 |

Comparative Example 1

The same cracking feedstock (VGO, with properties shown in Table 1) as in Example 1 was used in Comparative Example 1, with no radical initiator PHPG added. The micro-activity was evaluated under the same conditions as in Example 1. The evaluation results are shown in Table 2.

TABLE 2

Comparison of evaluation results of Examples 1-4 and Comparative Example 1

| Example No. | | Ex. 1 | Ex. 2 | Ex. 3 | Ex. 4 | Comp. Ex. 1 |
|---|---|---|---|---|---|---|
| Radical initiators | Type | PHPG | PHPG | PHPG | PHPG | None |
| | Weight average molecular weight | 10000 | 10000 | 10000 | 10000 | |
| | Degree of branching | 0.5 | 0.5 | 0.5 | 0.5 | |
| | Amount/ppm | 100 | 1000 | 2000 | 5000 | |
| Conversion/% | | 73.69 | 74.57 | 75.15 | 76.26 | 73.03 |
| Material balance/% | | | | | | |
| Dry gas | | 13.24 | 13.73 | 14.06 | 14.46 | 12.65 |
| Liquefied gas | | 27.44 | 28.05 | 28.45 | 28.95 | 24.33 |
| Gasoline | | 25.89 | 25.74 | 25.56 | 25.84 | 28.83 |
| Diesel oil | | 14.51 | 13.81 | 13.34 | 12.93 | 15.14 |
| Heavy oil | | 11.80 | 11.63 | 11.51 | 10.81 | 11.83 |
| Coke | | 7.12 | 7.04 | 7.08 | 7.01 | 7.22 |
| Ethylene yield/% | | 6.08 | 6.36 | 6.54 | 6.75 | 5.03 |
| Propylene yield/% | | 15.57 | 15.92 | 16.15 | 16.35 | 14.81 |
| Ethylene/propylene | | 0.390 | 0.399 | 0.405 | 0.413 | 0.340 |
| Butene yield/% | | 9.39 | 9.64 | 9.81 | 9.94 | 8.84 |

As can be seen from the data shown in Table 2, as compared to Comparative Example 1, after the addition of a macromolecular radical initiator to the cracking feedstock, the conversion of heavy oil in the catalytic cracking reaction is increased, the yield of liquefied gas is increased, the yield of coke is slightly decreased, and the yields of ethylene, propylene and butylene are increased. And the ethylene/propylene ratio in the product can be adjusted within a certain range by adjusting the amount of the radical initiator, so that the distribution of the ethylene/propylene in the product can be regulated.

Examples 5 to 9

A cracking feedstock (VGO, with properties shown in Table 1) was heated to 90° C. and 2000 ppm of a radical initiator PHPG was added and mixed uniformly. The molecular weight and degree of branching of the radical initiator PHPG are shown in Table 3.

The activity was evaluated on an activity evaluation device under the same conditions as in Example 1. The evaluation results are shown in Table 3.

TABLE 3

Comparison of evaluation results of Examples 3 and 5-9 with Comparative Example 1

| Example No. | | Ex. 3 | Ex. 5 | Ex. 6 | Ex. 7 | Ex. 8 | Ex. 9 | Comp. Ex. 1 |
|---|---|---|---|---|---|---|---|---|
| Radical initiators | Type | PHPG | PHPG | PHPG | PHPG | PHPG | PHPG | None |
| | Weight average Molecular weight | 10000 | 2000 | 5000 | 15000 | 20000 | 120000 | |
| | Degree of branching | 0.5 | 0.5 | 0.5 | 0.5 | 0.5 | 0.5 | |
| | Amount/ppm | 2000 | 2000 | 2000 | 2000 | 2000 | 2000 | |
| Conversion/% | | 75.15 | 75.03 | 75.23 | 75.34 | 75.54 | 75.15 | 73.03 |
| Material balance/% | | | | | | | | |
| Dry gas | | 14.06 | 13.56 | 14.05 | 14.23 | 14.5 | 13.98 | 12.65 |
| Liquefied gas | | 28.45 | 28.01 | 28.42 | 29.6 | 29.87 | 28.09 | 24.33 |
| Gasoline | | 25.56 | 26.25 | 25.53 | 24.36 | 24.12 | 25.83 | 28.83 |
| Diesel oil | | 13.34 | 13.30 | 13.15 | 13.21 | 13.11 | 13.33 | 15.14 |
| Heavy oil | | 11.51 | 11.67 | 11.62 | 11.45 | 11.35 | 11.52 | 11.83 |
| Coke | | 7.08 | 7.21 | 7.23 | 7.15 | 7.05 | 7.25 | 7.22 |
| Ethylene yield/% | | 6.54 | 6.04 | 6.23 | 6.75 | 6.81 | 6.15 | 5.03 |
| Propylene yield/% | | 16.15 | 15.12 | 15.83 | 16.42 | 16.49 | 15.11 | 14.81 |
| Ethylene/propylene | | 0.405 | 0.399 | 0.394 | 0.411 | 0.413 | 0.407 | 0.340 |
| Butene yield/% | | 9.81 | 9.35 | 9.69 | 9.95 | 9.99 | 9.42 | 8.84 |

As can be seen from the data shown in Table 3, after the addition of the radical initiator to the cracking feedstock, the conversion of heavy oil in the catalytic cracking reaction is increased, the yield of liquefied gas is increased, the yield of coke is maintained or slightly reduced, and the yields of ethylene, propylene and butylene are increased. The effect of the radical initiator on increasing catalytic cracking conversion, yield of light olefin, and ethylene/propylene ratio in the product is more pronounced when the preferred dendritic polymer and hyperbranched polymer of the present application each independently has a weight average molecular weight in the range of about 2000 to about 30000.

Examples 10 to 13

A cracking feedstock (VGO, with properties shown in Table 1) was heated to 90° C. and 2000 ppm of a radical initiator PHPG was added and mixed uniformly. The molecular weight and degree of branching of the radical initiator PHPG are shown in Table 4.

The micro-activity was evaluated on a micro-activity evaluation device under the same conditions as in Example 1. The evaluation results are shown in Table 4.

TABLE 4

Comparison of evaluation results of Examples 3 and 10-13 with Comparative Example 1

| Example No. | | Ex. 3 | Ex. 10 | Ex. 11 | Ex. 12 | Ex. 13 | Comp. Ex. 1 |
|---|---|---|---|---|---|---|---|
| Radical initiators | Type | PHPG | PHPG | PHPG | PHPG | PHPG | None |
| | Weight average molecular weight | 10000 | 10000 | 10000 | 10000 | 10000 | |
| | Degree of branching | 0.5 | 0.3 | 0.7 | 0.8 | 0.9 | |
| | Amount/ppm | 2000 | 2000 | 2000 | 2000 | 2000 | |
| Conversion/% | | 75.15 | 74.94 | 75.33 | 75.5 | 75.57 | 73.03 |
| Material balance/% | | | | | | | |
| Dry gas | | 14.06 | 13.83 | 14.11 | 14.32 | 14.51 | 12.65 |
| Liquefied gas | | 28.45 | 28.02 | 29.64 | 29.76 | 29.98 | 24.33 |
| Gasoline | | 25.56 | 26.03 | 24.55 | 24.31 | 24.05 | 28.83 |
| Diesel oil | | 13.34 | 13.51 | 13.08 | 13.12 | 13.04 | 15.14 |
| Heavy oil | | 11.51 | 11.55 | 11.59 | 11.38 | 11.39 | 11.83 |
| Coke | | 7.08 | 7.06 | 7.03 | 7.11 | 7.03 | 7.22 |
| Ethylene yield/% | | 6.54 | 6.31 | 6.59 | 6.80 | 6.82 | 5.03 |
| Propylene yield/% | | 16.15 | 15.56 | 16.17 | 16.39 | 16.5 | 14.81 |
| Ethylene/propylene | | 0.405 | 0.406 | 0.408 | 0.415 | 0.413 | 0.340 |
| Butene yield/% | | 9.81 | 9.75 | 9.85 | 9.94 | 9.98 | 8.84 |

As can be seen from the data shown in Table 4, after the addition of a macromolecular radical initiator to the cracking feedstock, the conversion of heavy oil in the catalytic cracking reaction is increased, the yield of liquefied gas is increased, the yield of coke is slightly reduced, and the yields of ethylene, propylene and butylene are increased. The effect of the radical initiator on increasing catalytic cracking conversion, yield of light olefin, and ethylene/propylene ratio in the product is more pronounced when the degrees of branching of the preferred dendritic polymer and hyperbranched polymer of the present application are each independently in the range of about 0.3-1.

Example 14

A cracking feedstock (VGO, with properties shown in Table 1) was heated to 90° C. and 2000 ppm of a radical initiator PHPG was added and mixed uniformly. The PHPG has a molecular weight of 11000 and a degree of branching of 0.5.

The micro-activity was evaluated on a micro-activity evaluation device under the same conditions as in Example 1. The evaluation results are shown in Table 5.

Example 15

A cracking feedstock (VGO, with properties shown in Table 1) was heated to 90° C. and 2000 ppm of a radical initiator hyperbranched polyamide-amine was added and mixed uniformly. The radical initiator hyperbranched polyamide-amine has a molecular weight of 10000, and a degree of branching of 0.5.

The micro-activity was evaluated on a micro-activity evaluation device under the same conditions as in Example 1. The evaluation results are shown in Table 5.

Example 16

A cracking feedstock (VGO, with properties shown in Table 1) was heated to 90° C. and 2000 ppm of a radical initiator dendritic polyamide-amine (PAMAM) (commercially available from Weihai CY Dendrimer Technology Co., Ltd. under the trade name PAMAM-G1) was added, which has a molecular weight of 5000 and a degree of branching of 1.

The micro-activity was evaluated on a micro-activity evaluation device under the same conditions as in Example 1. The evaluation results are shown in Table 5.

Example 17

A cracking feedstock (VGO, with properties shown in Table 1) was heated to 90° C. and 1000 ppm of a radical initiator dendritic polyamide-amine (PAMAM) (commercially available from Weihai CY Dendrimer Technology Co., Ltd. under the trade name PAMAM-G5, having a molecular weight of 25000, and a degree of branching of 1) and 1000 ppm of a radical initiator PHPG having a molecular weight of 5000 and a degree of branching of 1 were added.

The micro-activity was evaluated on a micro-activity evaluation device under the same conditions as in Example 1. The evaluation results are shown in Table 5.

TABLE 5

Comparison of evaluation results of Examples 3 and 14-17 with Comparative Example 1

| Example No. | | Ex. 3 | Ex. 14 | Ex. 15 | Ex. 16 | Ex. 17 | Comp. Ex. 1 |
|---|---|---|---|---|---|---|---|
| Radical initiators | Type | PHPG | PHPG | Self-made hyperbranched polyamide-amine | Commercially available dendritic polyamide-amines | Commercially available dendritic polyamide-amines and PHPG | None |
| | Weight average Molecular weight | 10000 | 11000 | 10000 | 5000 | 25000 and 5000 | |
| | Degree of branching | 0.5 | 0.5 | 0.5 | 1 | 1 | |
| | Amount/ppm | 2000 | 2000 | 2000 | 2000 | 2000(1:1) | |
| Conversion/% | | 75.15 | 75.49 | 75.77 | 74.93 | 75.24 | 73.03 |
| Material balance/% | | | | | | | |
| Dry gas | | 14.06 | 14.41 | 14.68 | 13.95 | 14.02 | 12.65 |
| Liquefied gas | | 28.45 | 29.68 | 30.11 | 28.22 | 29.63 | 24.33 |
| Gasoline | | 25.56 | 24.42 | 24.12 | 25.63 | 24.50 | 28.83 |
| Diesel oil | | 13.34 | 12.99 | 12.85 | 13.35 | 13.15 | 15.14 |
| Heavy oil | | 11.51 | 11.52 | 11.38 | 11.72 | 11.61 | 11.83 |
| Coke | | 7.08 | 6.98 | 6.86 | 7.13 | 7.09 | 7.22 |
| Ethylene yield/% | | 6.54 | 6.82 | 6.95 | 6.63 | 6.72 | 5.03 |
| Propylene yield/% | | 16.15 | 16.51 | 16.95 | 16.23 | 16.34 | 14.81 |
| Ethylene/propylene | | 0.405 | 0.413 | 0.410 | 0.409 | 0.411 | 0.340 |
| Butene yield/% | | 9.81 | 9.96 | 10.01 | 9.89 | 9.93 | 8.84 |

As can be seen from the data shown in Table 5, as compared to Comparative Example 1, after the addition of the radical initiator to the cracking feedstock, the conversion of heavy oil in the catalytic cracking reaction is increased, the yield of liquefied gas is increased, the ethylene/propylene ratio in the product is increased, the yield of coke is slightly decreased, and the yields of ethylene, propylene and butylene are increased. In addition, the addition of different types of radical initiators all provide good effects.

Example 18

2000 ppm of a radical initiator PHPG was added to a cracking feedstock (LCO, with properties shown in Table 6) and mixed uniformly. The PHPG has a molecular weight of 10000 and a degree of branching of 0.5.

The micro-activity evaluation was performed on a micro-activity evaluation device, under conditions including: a reaction temperature of 650° C., a regeneration temperature of 650° C., a catalyst-to-oil ratio of 1.28, a weight hourly space velocity of 16 h$^{-1}$, an MMC-2 equilibrium catalyst, and a catalyst load of 2 g. The evaluation results are shown in Table 7.

TABLE 6

Properties of the cracking feedstock used in Example 18 and Comparative Example 2

| Analyzing items | LCO |
|---|---|
| Density (20° C.)/(g · mL$^{-1}$) | 0.8149 |
| Sulfur/% | 0.05 |
| Nitrogen/% | 0.007 |
| Distillation range/° C. | |
| Initial boiling point | 225 |
| Final boiling point | 337 |

Comparative Example 2

The same cracking feedstock (LCO, with properties shown in Table 6) as Example 18 was used in Comparative Example 2, with no radical initiator PHPG added. The activity was evaluated under the same conditions as in Example 18. The evaluation results are shown in Table 7.

TABLE 7

Comparison of evaluation results of Example 18 and Comparative Example 2

| Example No. | | Example 18 | Comparative Example 2 |
|---|---|---|---|
| Radical initiator | Type | PHPG | None |
| | Weight average molecular weight | 10000 | |
| | Degree of branching | 0.5 | |
| | Amount/ppm | 2000 | |
| Conversion/% | | 58.74 | 57.29 |
| Material balance/% | | | |
| Dry gas | | 10.86 | 9.54 |
| Liquefied gas | | 32.15 | 30.45 |
| Gasoline | | 11.5 | 12.9 |
| Diesel oil | | 41.26 | 42.71 |
| Coke | | 4.23 | 4.4 |
| Ethylene yield/% | | 7.54 | 6.55 |
| Propylene yield/% | | 18.15 | 17.02 |
| Ethylene/propylene | | 0.415 | 0.385 |
| Butene yield/% | | 9.81 | 9.73 |

As can be seen from the data shown in Table 7, after the addition of a macromolecular radical initiator to the cracking feedstock (LCO), the conversion of heavy oil in the catalytic cracking reaction is increased, the yield of liquefied gas is increased, the yield of coke is slightly decreased, the yields of ethylene, propylene and butylene are increased, and the ethylene/propylene ratio is increased.

Example 19

2000 ppm of a radical initiator PHPG was added to a cracking feedstock (atmospheric column top straight run naphtha from Sinopec Yanshan Petrochemical Company, with properties shown in Table 8) and mixed uniformly. The PHPG has a molecular weight of 10000 and a degree of branching of 0.5.

The micro-activity evaluation was performed on a micro-activity evaluation device, under conditions including: a reaction temperature of 650° C., a regeneration temperature of 650° C., a catalyst-to-oil ratio of 1.28, a weight hourly space velocity of 16 $h^{-1}$, an MMC-2 equilibrium catalyst, and a catalyst load of 2 g. The evaluation results are shown in Table 9.

TABLE 8

Properties of the cracking feedstock used in Examples 19 to 20 and Comparative Examples 3 to 4

| Feedstock | Atmospheric column top straight run naphtha |
|---|---|
| Density (20° C.)/(g · $m^{-3}$) | 735.8 |
| Vapor pressure/kPa | 32 |
| Composition/m% | |
| Paraffins | 51.01 |
| N-alkanes | 29.40 |
| Cycloalkanes | 38.24 |
| Olefins | 0.12 |
| Aromatics | 10.52 |
| Distillation range/° C. | |
| Initial boiling point | 45.5 |
| 5% | 72.5 |
| 10% | 86.7 |
| 30% | 106.5 |
| 50% | 120.0 |
| 70% | 132.7 |
| 90% | 148.5 |
| 95% | 155.2 |
| Final boiling point | 166.5 |

Comparative Example 3

The same cracking feedstock (atmospheric column top straight run naphtha from Sinopec Yanshan Petrochemical Company, with properties shown in Table 8) as Example 19 was used in Comparative example 3, with no radical initiator PHPG added. The micro-activity was evaluated under the same conditions as in Example 19. The evaluation results are shown in Table 9.

Comparative Example 4-1

The same cracking feedstock as Example 19 (atmospheric column top straight run naphtha from Sinopec Yanshan Petrochemical Company, with properties shown in Table 8) was used in Comparative Example 4-1, with no radical initiator PHPG added.

The micro-activity evaluation was performed on a micro-activity evaluation device, under conditions including: a reaction temperature of 650° C., a regeneration temperature of 650° C., a catalyst-to-oil ratio of 1.28, a weight hourly space velocity of 16 $h^{-1}$, no catalyst added during the reaction, and 2 g of quartz sand packed in the reactor. The evaluation results are shown in Table 9.

Comparative Example 4-2

2000 ppm of a radical initiator PHPG was added to a cracking feedstock (atmospheric column top straight run naphtha from Sinopec Yanshan Petrochemical Company, with properties shown in Table 8) and mixed uniformly. The PHPG has a molecular weight of 10000 and a degree of branching of 0.5.

The micro-activity evaluation was performed on a micro-activity evaluation device, under conditions including: a reaction temperature of 650° C., a regeneration temperature of 650° C., a catalyst-to-oil ratio of 1.28, a weight hourly space velocity of 16 $h^{-1}$, no catalyst added during the reaction, and 2 g of quartz sand packed in the reactor. The evaluation results are shown in Table 9.

TABLE 9

Comparison of evaluation results of Example 19 and Comparative Examples 3 to 4

| Example No. | Comp. Ex. 3 | Ex. 19 | Increment | Comp. Ex. 4-1 | Comp. Ex. 4-2 | Increment |
|---|---|---|---|---|---|---|
| Conversion/% | 69.46 | 75.44 | 9.47% | 29.06 | 29.91 | 3.03% |
| Coke/% | 8.86 | 8.54 | | 8.86 | 8.54 | |
| Yield of liquid product/% | 30.54 | 24.56 | | 70.93 | 70.09 | |
| Yield of gaseous product/% | 60.60 | 66.9 | 11.39% | 20.21 | 21.37 | 5.74% |
| Yield of cracking gas product/% | | | | | | |
| $H_2$ | 0.75 | 0.72 | | 0.24 | 0.25 | |
| $C_1$ | 4.62 | 4.95 | | 1.56 | 1.58 | |
| $C_2^0$ | 3.39 | 3.78 | | 2.13 | 2.26 | |
| $C_2^-$ | 8.64 | 9.91 | 10.07% | 6.88 | 7.17 | 4.22% |
| $C_3^0$ | 2.46 | 2.85 | | 1.82 | 1.95 | |
| $C_3^-$ | 22.44 | 24.29 | 8.24% | 4.48 | 4.83 | 7.81% |
| n-$C_4^0$ | 1.53 | 2.01 | | 0.51 | 0.57 | |
| i-$C_4^0$ | 3.09 | 3.75 | | 1.03 | 1.15 | |

TABLE 9-continued

Comparison of evaluation results of Example 19 and Comparative Examples 3 to 4

| Example No. | Comp. Ex. 3 | Ex. 19 | Increment | Comp. Ex. 4-1 | Comp. Ex. 4-2 | Increment |
|---|---|---|---|---|---|---|
| $C_4^-$ | 13.68 | 14.64 | 7.02% | 1.56 | 1.61 | 3.21% |
| Ethylene/propylene | 0.385 | 0.408 | | 1.536 | 1.484 | |

As can be seen from the data shown in Table 9, in the presence of a catalyst, the reaction is mainly a catalytic cracking reaction, and after the addition of a radical initiator to the naphtha feedstock, the naphtha conversion in the catalytic cracking reaction is increased, the yield of gaseous product is increased, the yield of coke is slightly decreased, and the yields of ethylene, propylene and butylene are significantly increased.

In Comparative Example 4-1 and Comparative Example 4-2, no catalytic effect of acidic catalyst was involved, but thermal cracking reaction of naphtha occurred. As can be seen from the evaluation results, after the addition of a radical initiator to the naphtha feedstock, the thermal cracking reaction can be carried out at a relatively lower temperature, and the naphtha conversion can be increased, and the yields of ethylene, propylene and butylene can be improved; but when compared with Example 19, the promotion effect of a radical initiator alone is obviously inferior to that obtained in the catalytic cracking process, i.e. the effects of improving the catalytic cracking conversion, the yield of gaseous product, the yield of light olefins and the ethylene/propylene ratio in the products are better when the radical initiator and the catalytic cracking catalyst work together, which indicates that the radical initiator and the catalytic cracking catalyst have a certain synergistic effect, which may significantly promote the reaction for producing light olefins by catalytic cracking of naphtha.

Example 20

1000 ppm of a radical initiator PHPG was added to a cracking feedstock (atmospheric column top straight run naphtha from Sinopec Yanshan Petrochemical Company, with properties shown in Table 8) and mixed uniformly. The PHPG has a molecular weight of 10000 and a degree of branching of 0.5.

The micro-activity evaluation was performed on a micro-activity evaluation device, under conditions including: a reaction temperature of 650° C., a regeneration temperature of 650° C., a catalyst-to-oil ratio of 1.28, a weight hourly space velocity of 16 $h^{-1}$, an MMC-2 equilibrium catalyst, and a catalyst load of 2 g. The evaluation results are shown in Table 10.

Comparative Example 4-3

1000 ppm of a radical initiator PHPG was added to a cracking feedstock (atmospheric column top straight run naphtha from Sinopec Yanshan Petrochemical Company, with properties shown in Table 8) and mixed uniformly. The PHPG has a molecular weight of 10000 and a degree of branching of 0.5.

The micro-activity evaluation was performed on a micro-activity evaluation device, under conditions including: a reaction temperature of 650° C., a regeneration temperature of 650° C., a catalyst-to-oil ratio of 1.28, a weight hourly space velocity of 16 $h^{-1}$, no catalyst added during the reaction, and 2 g of quartz sand packed in the reactor. The evaluation results are shown in Table 10.

TABLE 10

Comparison of evaluation results of Example 20 and Comparative Examples 3 to 4

| Example No. | Comp. Ex. 3 | Ex. 20 | Increment | Comp. Ex. 4-1 | Comp. Ex. 4-3 | Increment |
|---|---|---|---|---|---|---|
| Conversion/% | 69.46 | 73.13 | 5.34% | 29.06 | 29.17 | 0.38% |
| Coke/% | 8.86 | 8.75 | | 8.86 | 8.78 | |
| Yield of liquid product/% | 30.54 | 26.83 | | 70.93 | 70.83 | |
| Yield of gaseous product/% | 60.60 | 64.42 | 6.30% | 20.21 | 20.39 | 0.89% |
| Yield of cracking gas product/% | | | | | | |
| $H_2$ | 0.75 | 0.75 | | 0.24 | 0.24 | |
| $C_1$ | 4.62 | 4.74 | | 1.56 | 1.57 | |
| $C_2^0$ | 3.39 | 3.56 | | 2.13 | 2.14 | |
| $C_2^-$ | 8.64 | 9.34 | 8.10% | 6.88 | 6.92 | 0.58% |
| $C_3^0$ | 2.46 | 2.76 | | 1.82 | 1.85 | |
| $C_3^-$ | 22.44 | 23.82 | 6.15% | 4.48 | 4.51 | 0.67% |
| $n-C_4^0$ | 1.53 | 1.76 | | 0.51 | 0.52 | |
| $i-C_4^0$ | 3.09 | 3.53 | | 1.03 | 1.05 | |
| $C_4^-$ | 13.68 | 14.16 | 3.51% | 1.56 | 1.59 | 1.92% |
| Ethylene/propylene | 0.385 | 0.392 | | 1.536 | 1.534 | |

As can be seen from the data shown in Table 10, in the presence of a catalyst, the catalytic cracking reaction of naphtha is significantly promoted by adding only 1000 ppm of a radical initiator PHPG, the naphtha conversion in the catalytic cracking reaction is increased, the yield of gaseous product is increased, the yield of coke is slightly reduced, and the yields of ethylene, propylene and butylene are significantly increased. In the absence of a catalyst, the effect of the radical initiator PHPG added in an amount of only 1000 ppm on thermal cracking of naphtha is very weak. The results further prove that the radical initiator and the catalytic cracking catalyst have a certain synergistic effect, so that the reaction for producing light olefins by catalytic cracking can be significantly promoted by adding only a very small amount of the radical initiator, while the same amount of radical initiator has basically no effect on promoting the thermal cracking reaction.

Example 21

2000 ppm of a radical initiator PHPG was added to a cracking feedstock (n-octane, analytically pure (AR)) and mixed uniformly. The PHPG has a molecular weight of 10000 and a degree of branching of 0.5.

The micro-activity evaluation was performed on a micro-activity evaluation device, under conditions including: a reaction temperature of 650° C., a regeneration temperature of 650° C., a catalyst-to-oil ratio of 1.28, a weight hourly space velocity of 16 h$^{-1}$, an MMC-2 equilibrium catalyst, and a catalyst load of 2 g. The evaluation results are shown in Table 11.

Comparative Example 5

The same cracking feedstock (n-octane, AR) as in Example 21 was used in Comparative Example 5, with no radical initiator PHPG added. The micro-activity was evaluated under the same conditions as in Example 21. The evaluation results are shown in Table 11.

TABLE 11

Comparison of evaluation results of Example 21 and Comparative Example 5

| Example No. | Comp. Ex. 5 | Ex. 21 |
| --- | --- | --- |
| Conversion/% | 64.51 | 67.24 |
| Coke/% | 3.13 | 3.09 |
| Yield of liquid product/% | 46.45 | 42.91 |
| Yield of gaseous product/% | 50.42 | 54.00 |
| Yield of cracking gas product/% | | |
| $H_2$ | 0.23 | 0.25 |
| $C_1$ | 2.10 | 2.79 |
| $C_2^0$ | 4.07 | 4.95 |
| $C_2^-$ | 9.51 | 11.78 |
| $C_3^0$ | 4.92 | 3.71 |
| $C_3^-$ | 16.93 | 17.39 |
| $n-C_4^0$ | 2.43 | 2.23 |
| $i-C_4^0$ | 3.14 | 3.34 |
| $C_4^-$ | 7.09 | 7.56 |
| Ethylene/propylene | 0.562 | 0.677 |

As can be seen from the data shown in Table 11, after the addition of a macromolecular radical initiator to the n-octane feedstock, the conversion in the catalytic cracking reaction is increased, the yield of gaseous product is increased, the ethylene/propylene ratio in the product is increased, the yield of coke is slightly reduced, and the yields of ethylene, propylene and butylene are increased.

Example 22

2000 ppm of a radical initiator PHPG was added to a cracking feedstock (n-octane, AR) and mixed uniformly. The PHPG has a molecular weight of 10000 and a degree of branching of 0.5.

The micro-activity evaluation was performed on a micro-activity evaluation device, under conditions including: a reaction temperature of 550° C., a regeneration temperature of 650° C., a catalyst-to-oil ratio of 1.28, a weight hourly space velocity of 16 h$^{-1}$, an MMC-2 equilibrium catalyst, and a catalyst load of 2 g. The evaluation results are shown in Table 12.

Comparative Example 6

The same cracking feedstock (n-octane, AR) as in Example 22 was used in Comparative Example 6, with no radical initiator PHPG added. The micro-activity was evaluated under the same conditions as in Example 22. The evaluation results are shown in Table 12.

Comparative Example 7-1

The same cracking feedstock (n-octane, AR) as in Example 22 was used in Comparative Example 7-1, with no radical initiator PHPG added.

The micro-activity evaluation was performed on a micro-activity evaluation device, under conditions including: a reaction temperature of 550° C., a regeneration temperature of 650° C., a catalyst-to-oil ratio of 1.28, a weight hourly space velocity of 16 h$^{-1}$, no catalyst added during the reaction, and 2 g of quartz sand packed in the reactor. The evaluation results are shown in Table 12.

Comparative Examples 7-2

2000 ppm of a radical initiator PHPG was added to a cracking feedstock (n-octane, AR) and mixed uniformly. The PHPG has a molecular weight of 10000 and a degree of branching of 0.5.

The micro-activity evaluation was performed on a micro-activity evaluation device, under conditions including: a reaction temperature of 550° C., a regeneration temperature of 650° C., a catalyst-to-oil ratio of 1.28, a weight hourly space velocity of 16 h$^{-1}$, no catalyst added during the reaction, and 2 g of quartz sand packed in the reactor. The evaluation results are shown in Table 12.

TABLE 12

Comparison of evaluation results of Example 22 and Comparative Examples 6 to 7

| Example No. | Comp. Ex. 6 | Ex. 22 | Increment | Comp. Ex. 7-1 | Comp. Ex. 7-2 | Increment |
|---|---|---|---|---|---|---|
| Conversion/% | 38.7 | 48.64 | 25.68% | 14.88 | 14.92 | 0.30% |
| Coke/% | 1.09 | 1.11 | | 1.16 | 1.20 | |
| Yield of liquid product/% | 70.41 | 62.18 | | 90.12 | 90.00 | |
| Yield of gaseous product/% | 28.5 | 36.71 | 28.81% | 8.72 | 8.80 | 0.93% |
| Yield of cracking gas product/% | | | | | | |
| $H_2$ | 0.09 | 0.11 | | 0.05 | 0.05 | |
| $C_1$ | 0.25 | 0.3 | | 0.65 | 0.66 | |
| $C_2^0$ | 1.33 | 1.61 | | 1.25 | 1.27 | |
| $C_2^=$ | 2.99 | 4.13 | 38.13% | 2.29 | 2.30 | 0.59% |
| $C_3^0$ | 5.33 | 8.44 | | 0.20 | 0.21 | |
| $C_3^=$ | 8.57 | 10.72 | 25.09% | 2.52 | 2.54 | 0.90% |
| n-$C_4^0$ | 3.34 | 3.94 | | 0.09 | 0.10 | |
| i-$C_4^0$ | 0.63 | 1.14 | | 0.01 | 0.02 | |
| $C_4^=$ | 5.97 | 6.32 | 5.86% | 1.66 | 1.65 | -0.72% |
| Ethylene/propylene | 0.35 | 0.39 | | 0.19 | 0.19 | |

As can be seen from the data shown in Table 12, the conversion of n-octane cracking is low at a low temperature, especially in the absence of a catalyst. In the presence of a catalyst, after the addition of 2000 ppm of a radical initiator PHPG, the catalytic cracking reaction of n-octane is significantly promoted, the conversion of n-octane in the catalytic cracking reaction is improved, the yield of gaseous product is increased, the yield of coke is basically maintained, and the yields of ethylene, propylene and butylene are significantly improved. In addition, in the absence of a catalyst, the addition of the radical initiator PHPG has basically no effect on promoting the thermal cracking reaction of n-octane at a low temperature. The results further prove that the radical initiator and the catalytic cracking catalyst have a certain synergistic effect, so that the reaction for producing light olefins by catalytic cracking can be significantly promoted at a low temperature, while the same amount of radical initiator has basically no effect on promoting the thermal cracking reaction at the same temperature.

The present application is illustrated in detail hereinabove with reference to preferred embodiments, but is not intended to be limited to those embodiments. Various modifications may be made following the inventive concept of the present application, and these modifications shall be within the scope of the present application.

It should be noted that the various technical features described in the above embodiments may be combined in any suitable manner without contradiction, and in order to avoid unnecessary repetition, various possible combinations are not described in the present application, but such combinations shall also be within the scope of the present application.

In addition, the various embodiments of the present application can be arbitrarily combined as long as the combination does not depart from the spirit of the present application, and such combined embodiments should be considered as the disclosure of the present application.

The invention claimed is:

1. A catalytic cracking process for producing light olefins, comprising a step of contacting a cracking feedstock with a catalytic cracking catalyst in the presence of a radical initiator for reaction under catalytic cracking conditions to obtain a product comprising light olefins, wherein the radical initiator comprises a dendritic polymer, a hyperbranched polymer or a combination thereof, the catalytic cracking catalyst comprises a Y zeolite, a shape selective zeolite, or a combination thereof, and the cracking feedstock is selected from the group consisting of hydrocarbons having 4-14 carbon atoms, naphtha, light cycle oil, vacuum gas oil, vacuum residuum, and combinations thereof.

2. The process according to claim 1, wherein the dendritic polymer and the hyperbranched polymer are each independently selected from the group consisting of polyolefins, polyetheresters, polyethers, polyurethanes, polyamides, polysilanes, and combinations thereof.

3. The process according to claim 1, wherein the radical initiator comprises a polymer selected from the group consisting of hyperbranched polyglycidyl ethers, terminal group-modified hyperbranched polyglycidyl ethers, dendritic polyamide-amines, hyperbranched polyamide-amines, and combinations thereof.

4. The process according to claim 1, wherein the radical initiator comprises a terminal group-modified hyperbranched polyglycidyl ether, the terminal group of which being selected from the group consisting of ester groups having 2-10 carbon atoms, amine group, mercapto group, and combinations thereof.

5. The process according to claim 1, wherein the dendritic polymer and the hyperbranched polymer each independently has a degree of branching of 0.3-1.

6. The process according to claim 1, wherein the dendritic polymer and the hyperbranched polymer each independently has a weight average molecular weight of from 2000 to 30000.

7. The process according to claim 1, wherein the radical initiator comprises a palmitate-terminated hyperbranched polyglycidyl ether (PHPG) having a weight average molecular weight of 1000-30000 and a degree of branching of 0.3-1.

8. The process according to claim 7, wherein the palmitate-terminated hyperbranched polyglycidyl ether (PHPG) has a structure represented by formula (I):
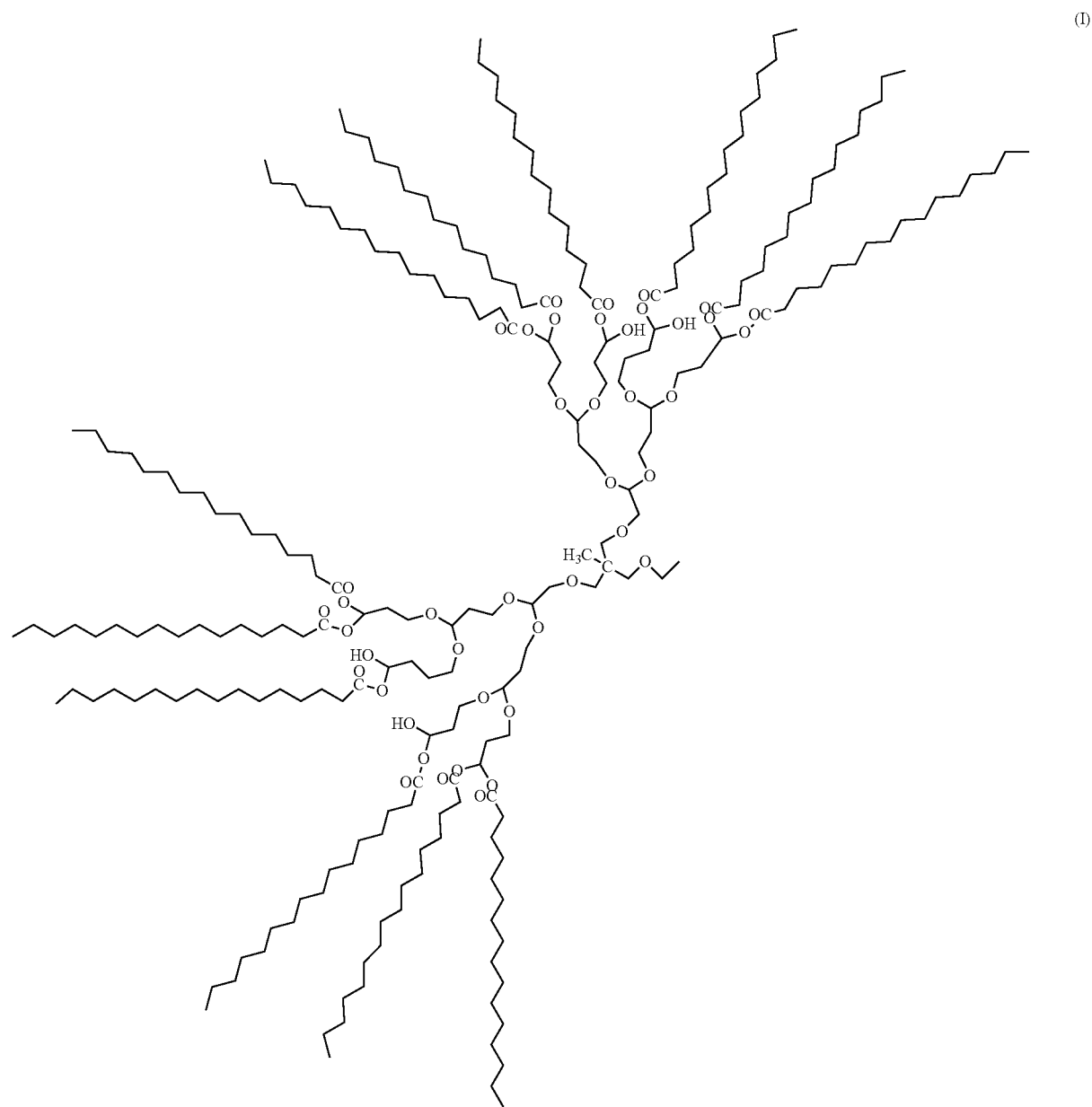

-continued

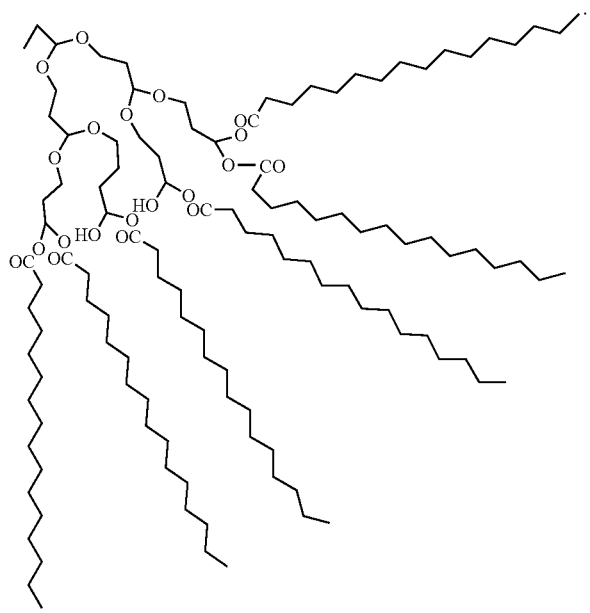

9. The process according to claim 1, wherein the shape selective zeolite is selected from the group consisting of ZSM-5 zeolite, β zeolite, and combinations thereof.

10. The process according to claim 1, wherein the ratio of the total weight of dendritic polymer and hyperbranched polymer contained in the radical initiator to the weight of the cracking feedstock is 0.00001:1 to 0.01:1.

11. The process according to claim 1, wherein the catalytic cracking conditions include:
a reaction temperature of 450-700° C.;
a weight hourly space velocity of 1-50 $h^{-1}$; and
a catalyst-to-oil ratio of 1:1 to 20:1.

12. The process according to claim 1, wherein the radical initiator comprises a palmitate-terminated hyperbranched polyglycidyl ether (PHPG) having a weight average molecular weight of 2000-20000, and a degree of branching of 0.3-0.9.

* * * * *